United States Patent

Ashbrook et al.

[11] 4,012,410
[45] Mar. 15, 1977

[54] 2-(4-METHOXYOXAZOLIDINONE-4-YL)THIAZOLIDINE T-BUTYL ESTERS

[75] Inventors: Charles W. Ashbrook, Greenwood; Gary V. Kaiser; Gary A. Koppel, both of Indianapolis, all of Ind.

[73] Assignee: Eli Lilly and Company, Indianapolis, Ind.

[22] Filed: Apr. 14, 1975

[21] Appl. No.: 568,070

Related U.S. Application Data

[62] Division of Ser. No. 222,294, Jan. 31, 1972, abandoned.

[52] U.S. Cl. .................... 260/306.7 C; 260/239.1; 424/271
[51] Int. Cl.² .................................. C07D 419/00
[58] Field of Search ................ 260/306.7 C

[56] References Cited
UNITED STATES PATENTS 2,555,008  5/1951  Rolfson et al. ............ 260/306.7 C

*Primary Examiner*—R. J. Gallagher
*Attorney, Agent, or Firm*—William B. Scanlon; Everet F. Smith

[57] ABSTRACT

6-acylamido-6-methoxypenicillanic acids are obtained by reacting a 6-acylamidopenicillanic acid with mercuric acetate in methanol to yield a methyl α-methoxypenicilloate. Esterification of the latter with isobutylene affords the methyl, t-butyl diester of the methoxypenicilloic acid which undergoes selective hydrolysis in base to provide the free α-carboxylic acid half t-butyl ester of the penicilloic acid. The latter on reaction with dicyclohexylcarbodiimide affords an oxazolone-thiazolidine of the formula

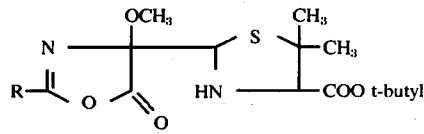

which with 98% formic acid provides a compound of the invention.

2 Claims, No Drawings

2-(4-METHOXYOXAZOLIDINONE-4-YL)THIAZOLIDINE T-BUTYL ESTERS

This is a division of application Ser. No. 222,294 filed Jan. 31, 1972, now abandoned.

BACKGROUND OF THE INVENTION

This invention relates to new penicillin antibiotics. In particular, this invention relates to 6-acylamido-6-methoxypenicillanic acids and to intermediates useful in the preparation thereof.

Since the discovery of penicillin numerous semisynthetic penicillins have been prepared by the acylation of the penicillin nucleus, 6-aminopenicillanic acid. Thus far the structural modification of the basic penicillin molecule has involved almost exclusively variations of the 6-acylamido side chain.

The preparation of a methoxy substituted penicilloic acid by the reaction of benzyl penicillin with mercuric acetate in methanol has been reported by O. Wintersteiner and H. E. Stavely, (H. T. Clarke, J. R. Johnson, and R. Robinson, eds., *The Chemistry of Penicillin*, Princeton University Press, Princeton, N.J. 1949, at page 222). F. H. Carpenter et al. have reported a two-step reaction sequence for the preparation of synthetic penicillins, *J. Biol. Chem.*, 176, 915 (1948). In the first step of the sequence, a substituted oxazolone is reacted with an α-amino-β-mercapto acid to provide a penicillenic acid. The penicillenic acid is then heated in pyridine in the presence of pyridine hydrochloride to provide, in low yield, a synthetic penicillin. However, substituted penicillins other than 6-acylamido-substituted penicillins are not disclosed.

It is an object of this invention to provide 6-methoxypenicillanic acids and certain oxazolone-thiazolidines as intermediates useful in the preparation thereof.

SUMMARY OF THE INVENTION

The 6-methoxypenicillins provided by this invention are represented by the following general formula.

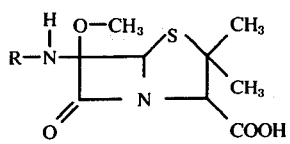

In the above formula R is the organic acyl portion of a penicillin side chain. For example R represents the acyl moiety of the well known penicillin side chains which have been extensively described in the prior art. For example, R represents acetyl, propionyl, 2,6-dimethoxybenzoyl, phenylacetyl, phenoxyacetyl, phenylglycyl, mandelyl, 2-thiopheneacetyl, 2-furylacetyl, and the like acyl radicals.

The penicillin ethers of the above general formula are prepared by reacting a 6-acylamidopenicillanic acid with mercuric acetate in the presence of methanol to provide the methoxylated penicilloic acid methyl ester of the formula

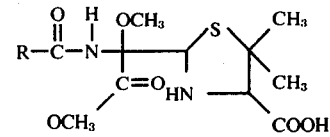

The penicilloic acid methyl ester is reacted in the presence of acid with isobutylene to produce the tertiarybutyl ester of the carboxyl group of the thiazolidine ring. Selective hydrolysis of the methyl penicilloate affords the methoxylated penicilloic acid half t-butyl ester, represented by the following formula.

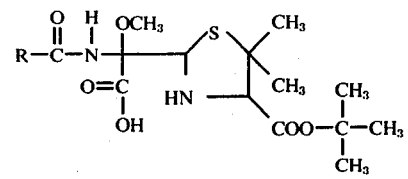

The penicilloic acid half ester thus obtained is reacted under anhydrous conditions with dicyclohexylcarbodiimide to provide, via intramolecular cylization involving the free α-carboxyl group, a methoxylated oxazolone-thiazolidine represented by the following formula.

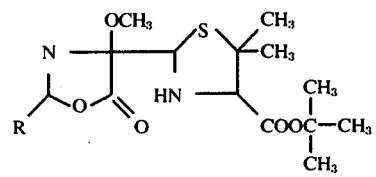

The methoxylated oxazalone is reacted with 98% formic acid under substantially anhydrous conditions to provide a 6-acylamido-6-methoxypenicillanic acid.

The methoxy penicillins provided by this invention display significant antimicrobial activity. In particular, the methoxylated penicillins are useful in combatting infections caused by the gram-positive organisms.

DETAILED DESCRIPTION OF THE INVENTION

The new penicillin antibiotics provided by this invention are represented in more detail by the following Formula I.

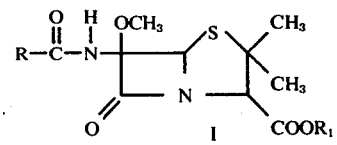

wherein R is $C_1$–$C_6$ alkyl, phenyl, substituted phenyl, or a group represented by the formula

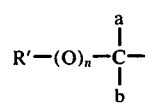

wherein

R' is α-thienyl, β-thienyl, α-furyl, β-furyl, phenyl, or substituted phenyl, n is 0 or 1, a is hydrogen or $C_1$–$C_3$ alkyl, b is hydrogen, $C_1$–$C_3$ alkyl, hydroxy, amino or protected amino; with the limitation that when n is 1, R' is phenyl or substituted phenyl and b is hydrogen or $C_1$–$C_3$ alkyl;

$R_1$ is hydrogen, $C_1$–$C_4$ alkyl, benzyl, or benzhydryl.

In the foregoing definition the term, "$C_1$–$C_6$ alkyl", refers to the alkyl hydrocarbon radicals having from 1 to 6 carbon atoms such as methyl, ethyl, n-propyl, iso-propyl, n-butyl, sec-butyl, n-amyl, iso-amyl, n-hexyl, and the like. Similarly, the terms, "$C_1$–$C_4$ lower alkyl" and "$C_1$–$C_3$ lower alkyl" refer to the alkyl hydrocarbon radicals possessing respectively from 1 to 4 and from 1 to 3 carbon atoms.

The term, "substituted phenyl", has reference to halophenyl such as 4-chlorophenyl, 4-bromophenyl, 3,4-dichlorophenyl, 2,6-dichlorophenyl, 3-chlorophenyl and like mono and di-halogenated phenyl rings; to $C_1$–$C_4$ lower alkylphenyl such as 4-methylphenyl, 4-isopropylphenyl, 4-t-butylphenyl, 3,4-dimethylphenyl and the like; to $C_1$–$C_4$ lower alkoxyphenyl, such as 4-methoxyphenyl, 3-methoxy-4-ethoxyphenyl, 3,4-dimethoxyphenyl, 2,6-dimethoxyphenyl, 4-isopropoxyphenyl, 4-n-butoxyphenyl and the like; and to hydroxyphenyl such as 4-hydroxyphenyl, 3,4-dihydroxyphenyl and the like.

The term, "protected amino", has reference to the primary amino group which is substituted by one of the commonly employed amino-protecting groups which are readily removable and used to protect the reactive amino function during a reaction sequence. Such groups are commonly employed and understood in the art and include for example, t-butyloxycarbonyl, 2,2,2-trichloroethoxycarbonyl, ethoxycarbonyl, and benzyloxycarbonyl. The nature of the protecting group is unimportant in the present invention so long as the protecting group will survive the reaction conditions herein delineated for preparing the compounds of the invention. Accordingly, the particular protecting group should be substantially stable in the presence of mercuric acetate and should survive the basic hydrolysis conditions employed in the hydrolysis of the methyl penicilloate.

The following compounds are illustrative of the compounds represented by the Formula I 6-acetamido-6-methoxypenicillanic acid,
6-propionamido-6-methoxypenicillanic acid,
6-n-hexamido-6-methoxypenicillanic acid,
6-n-heptamido-6-methoxypenicillanic acid,
6-benzamido-6-methoxypenicillanic acid,
t-butyl 6-acetamido-6-methoxypenicillanate,
methyl 6-propionamido-6-methoxypenicillanate,
6-(2-phenylacetamido)-6-methoxypenicillanic acid,
6-(2-phenoxyacetamido)-6-methoxypenicillanic acid,
t-butyl 6-(2-phenoxyacetamido)-6-methoxypenicillanate,
benzyl 6-(2-phenylacetamido)-6-methoxypenicillanate,
6-[2(2-thienyl)acetamido]-6-methoxypenicillanic acid,
6[2-(3-thienyl)acetamido]-6-methoxypenicillanic acid,
benzhydryl 6-[2(2-thienyl)acetamido]-6-methoxypenicillanate,
6-[2(2-furyl)acetamido]-6-methoxypenicillanic acid,
6-(2,6-dimethoxybenzamido)-6-methoxypenicillanic acid,
6-(2-amino-2-phenylacetamido)-6-methoxypenicillanic acid,
6-(2,2-dimethyl-2-phenylacetamido)-6-methoxypenicillanic acid,
6-(2-hydroxy-2-phenylacetamido)-6-methoxypenicillanic acid,
6-[2-(3-hydroxyphenyl)acetamido]-6-methoxypenicillanic acid,
6-(2-t-butyloxycarbamido-2-phenylacetamido)-6-methoxypenicillanic acid,
t-butyl 6-(2,2-dimethyl-2-phenylacetamido)-6-methoxypenicillanate,
benzyl 6-[2-(4-hydroxyphenyl)acetamido]-6-methoxypenicillanate.

The 6-methoxypenicillins of the Formula I are prepared with the corresponding unsubstituted 6-acylamidopenicillanic acids. Initially, the starting penicillin is reacted with four equivalents of mercuric acetate in methanol to provide the α-methoxy-α-monoethylester of the corresponding penicilloic acid according to the procedure described by H. T. Clarke, J. R. Johnson and R. Robinson, eds. *The Chemistry of Penicillin*, Princeton University Press, Princeton, N. J. 1949, at page 222. The free carboxyl group attached to the thiazolidine ring of the methyl penicilloate is then protected by esterification. Esters which are stable under base hydrolysis conditions are preferred, and in particular, the t-butyl ester is preferred. Such esters as the benzyl, benzhydryl and methyl are less desirable but can be employed in the present process.

The t-butyl ester, the preferred carboxylic acid protecting ester group of this invention, is prepared by reacting the methyl penicilloate with isobutylene in the presence of an acid in an inert solvent to obtain the diester of the penicilloic acid. The preparation of the tertiary butyl ester is desirably carried out in the following manner.

The methyl penicilloate is dissolved in a mixture of dioxane and 10% sulfuric acid contained in a pressure bottle. The solution is cooled to a temperature between about −30° and −15° C. and an excess of isobutylene is added to the solution. The reaction vessel is then capped so as to maintain a positive pressure of isobutylene. The reaction vessel is shaken for a period of about 12 hours to insure completion of the esterification reaction. Thereafter, the reaction vessel is vented and the reaction mixture is poured into a cold mixture of ethyl acetate and 1N sodium hydroxide. The aqueous phase is separated and extracted with ethyl acetate and the extracts are combined with the organic phase. The organic phase is washed with cold water, dried, and evaporated under vacuum to yield the penicilloic acid diester as an oily residue. The methyl t-butyl ester thus prepared can be further purified by chromatography.

The diester is then hydrolyzed with base to effect the selective hydrolysis of the α-methyl ester of the penicilloic acid diester to provide the free α-carboxylic acid represented by the following structural formula.

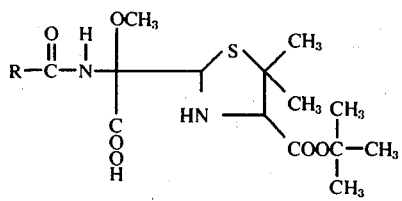

The basic hydrolysis of the α-methyl ester is carried out by reacting the diester with one equivalent of a base such as sodium hydroxide or potassium hydroxide in an aqueous medium such as aqueous methanol, aqueous ethanol, or preferably aqueous dioxane. The hydrolysis is carried out in the cold and preferably at or about 0°–5° C. for about 10–15 hours. The hydrolysis mixture is diluted with water and is then freeze-dried to provide the mono sodium salt of the penicilloic acid half t-butyl ester as a crude solid. The crude salt is dissolved in water and the solution layered with ethyl acetate. The mixture is then cooled to 5° C. in an ice-bath and is acidified with 0.1N hydrochloric acid with stirring. The organic layer is separated and the aqueous layer is extracted with ethyl acetate. The ethyl acetate extracts are combined, washed with water and dried. The dried extract is evaporated to dryness to provide the methoxylated penicilloic acid half t-butyl ester.

The penicilloic acid half ester thus obtained is reacted with dicyclohexylcarbodiimide at a temperature between about −90° and −20° C. and preferably at −80° C. in an inert dry solvent and preferably a halogenated hydrocarbon solvent such as dichloromethane, to provide the methoxylated oxazalone t-butyl ester of the following Formula II.

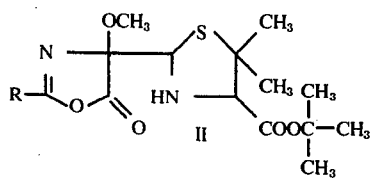

wherein R has the same meanings as defined in Formula I.

The compounds represented by the above Formula II are formally named as t-butyl 2-[4-methoxy-5-oxo-2-(arylmethyl, phenoxymethyl or alkyl)-2-oxazolin-4-yl]-5,5-dimethyl-4-thiazolidinecarboxylates wherein aryl refers to phenyl, 2-thienyl, 3-thienyl, 2-furyl, 3-furyl or phenyl. However, for convenience the compounds of Formula II are referred to herein as methoxyoxazolone-thiazolidines.

Illustrative of the compounds represented by the Formula II are the following:

t-butyl 2-[4-methoxy-5-oxo-2-(phenoxymethyl)-2-oxazolin-4-yl]-5,5-dimethyl-4-thiazolidinecarboxylate, t-butyl 2-[4-methoxy-5-oxo-2-(phenylmethyl)-2-oxazolin-4-yl]-5,5-dimethyl-4-thiazolidinecarboxylate, t-butyl 2-[4-methoxy-5-oxo-2-methyl-2-oxazolin-4-yl]-5,5-dimethyl-4-thiazolidinecarboxylate, t-butyl 2-[4-methoxy-5-oxo-2-(α-hydroxyphenylmethyl)-2-oxozolin-4-yl]-5,5-dimethyl-4-thiazolidinecarboxylate, t-butyl 2-[4-methoxy-5-oxo-2-(2-thienylmethyl)-2-oxazolin-4-yl]-5,5-dimethyl-4-thiazolidinecarboxylate, t-butyl 2-[4-methoxy-5-oxo-2-(3-hydroxyphenylmethyl)-2-oxazolin-4-yl]-5,5-dimethyl-4-thiazolidinecarboxylate, t-butyl 2-[4-methoxy-5-oxo-2-(α-aminophenylmethyl)-2-oxazolin-4-yl]-5,5dimethyl-4-thiazolidinecarboxylate, t-butyl 2-[4-methoxy-5-oxo-2-ethyl-2-oxazolin-4-yl]-5,5-dimethyl-4-thiazolidinecarboxylate, t-butyl 2-[4-methoxy-5-oxo-2-(3,4-dichlorophenylmethyl)-2-oxazolin-4-yl]-5,5-dimethyl-4-thiazolidinecarboxylate, and t-butyl 2-[4-methoxy-5-oxo-2-(2,6-dimethoxyphenylmethyl)-2-oxazolin-4-yl]-5,5-dimethyl-4-thiazolidinecarboxylate.

The methoxy oxazolone can be isolated from the reaction mixture and then converted by reaction with 98% formic acid to provide, via cleavage of the oxazolone ring and subsequent β-lactam ring formation, a 6-acylamido-6-methoxypenicillanic acid.

The reaction of the methoxyoxazolone-thiazolidine with 98% formic acid is carried out at a temperature between about 15° and 30° C. and most conveniently at room temperature. The oxazoline is mixed with an excess of the 98% formic acid and the mixture is stirred for about 30 minutes to about one hour.

Alternatively, the oxazolone can be reacted, without isolation, with 98% formic acid to provide directly the 6-acylamido-6-methoxypenicillanic acid.

During the reaction of the oxazolone with formic acid, β-lactam ring formation occurs concurrently with t-butyl ester hydrolysis, to provide the 6-methoxypenicillanic acid.

When the reaction with formic acid is carried out in less than 30 minutes, particularly at temperatures below room temperature, the hydrolysis of the t-butyl ester is often incomplete and the reaction mixture contains both the 6-methoxy-6-acylamidopenicillanic acid and t-butyl 6-methoxy-6-acylamidopenicillanate as well as some unreacted starting material. The mixture thus obtained can be recycled to complete the reaction.

The penicillins thus prepared are recovered from the reaction mixture by first neutralizing the excess formic acid and thereafter extracting the penicillin with an organic solvent such as ethyl acetate or isoamyl acetate. Alternatively, the penicillanic acid reaction product can be converted to a salt such as the sodium salt, and this salt can be extracted with an aqueous wash from the dichloromethane reaction solvent. The salt can then be acidified to provide the free penicillanic acid in the conventional manner.

The 6-methoxy-6-acylamidopenicillanic acid thus recovered from the reaction mixture can be purified by chromatography over silica gel adsorbent.

The 6-methoxy-6-acylamidopenicillanic acids provided by this invention are useful antibiotic compounds which can be employed in combatting bacterial infections. The compounds of the invention display antimicrobial activity similar to that of the corresponding non-methoxylated 6-acylamidopenicillanic acids. For example, the compounds of the invention inhibit the growth of gram-positive organisms, for example, *Staphylococcus aureus, Bacillus subtilis* and *Sarcina lutea.* They also exhibit activity against the gram-negative organisms. However, in general, higher concentrations of the compounds are required in comparison with the concentrations required to control the gram-positive organisms. Illustrative of the gram-negative organisms against which the compounds of the invention have demonstrated activity are *Proteus vulgaris, Escherichia coli* and *Klebsiella pneumoniae*. Accordingly, when administered to warm blooded mammals at a dose between about 2.5 and 250 mg./kg. the compounds of the invention are useful in combatting infections attributable to infectious staphylococcus and streptococcus organisms. The compounds of the invention are relatively non-toxic substances and in general their toxicity approximates that of the corresponding nonmethoxylated penicillins.

When in the Formula I, $R_1$ is $C_1$–$C_4$ alkyl, benzyl or benzhydryl, the penicillin esters represented are useful intermediates in the preparation of the antibiotic penicillin acids wherein $R_1$ is hydrogen. The esters can be readily cleaved by known procedures to provide the free carboxylic acid.

The following examples more fully illustrate the compounds and procedures of the present invention.

EXAMPLE 1

Preparation of 6-phenoxyacetamido-6-methoxypenicillanic acid

To a solution of 3.5 g. (10 mmole.) of 6-(2-phenoxyacetamido)penicillanic acid in 160 ml. of absolute methanol was added at room temperature in one portion a solution of 12.7 g. of mercuric acetate in 150 ml. of absolute methanol. The reaction mixture was stirred at room temperature for 30 minutes during which time a precipitate of mercurous acetate had formed. The reaction mixture was then treated with hydrogen sulfide gas until the formation of a precipitate of mercuric sulfide had ceased. The precipitate was filtered through a charcoal filter and the filtrate was evaporated in vacuo to an oil. The oil was dissolved in ethyl acetate and the solution was washed twice with 50 ml. portions of a saturated solution of sodium bicarbonate and twice with 50 ml. portions of water. The washed solution was then dried and the solvent evaporated in vacuo to yield 3.2 g. of 2-[methoxy(methoxycarbonyl)(2-phenoxyacetamido)methyl]-5,5-dimethyl-4-thiazolidinecarboxylic acid.

The acid was dissolved in ether and the ethereal solution treated with diazomethane to prepare methyl 2-[methoxy(methoxycarbonyl)(2-phenoxyacetamido)-methyl]-5,5-dimethyl-4-thiazolidinecarboxylate, which on recrystallization from a solvent mixture of 5 ml. of ethyl acetate and 25 ml. of n-hexane has a melting point of about 129° to 130° C. Elemental analysis of the dimethyl ester of the penicilloic acid thus prepared gave the following percentage elemental composition.

Theory: C, 53.57; H, 6.15; N, 6.57; S, 7.52. Found: C, 53.81; H, 6.32; N, 6.42; S, 7.45.

Methoxyl determination: Theory: 21.81. Found: 22.10.

To a solution of 4.12 g. of the penicilloic acid half methyl ester prepared as described above in 25 ml. of dioxane containing 2.5 ml of concentrated sulfuric acid was added 25 ml. of liquid isobutylene at a temperature of −20° C. The cold reaction solution was placed in a pressure bottle and shaken at room temperature overnight. The reaction mixture was poured into a cold mixture of 200 ml. of ethyl acetate and 125 ml. of 1 N sodium hydroxide. The aqueous phase was separated and was extracted repeatedly with ethyl acetate. The extracts were combined and washed with water. The washed extracts were then dried and thereafter evaporated in vacuo to provide 3.22 g. of a yellow oil. A thin layer chromatogram of the yellow oil showed the oil to be two spot material. The oily residue was then chromatographed over silica gel by the gradient elution technique employing benzene and ethyl acetate as the gradient. The fractions collected when the gradient comprised from about 14 to 15.5% ethyl acetate were combined and evaporated in vacuo to yield a semi-solid residue. The residue was recrystallized from hexane containing a very minor amount of ethyl acetate to yield t-butyl 2-[methoxy(methoxycarbonyl)(2-phenoxyacetamido)methyl]-5,5-dimethyl-4-thiazolidinecarboxylate as a white crystalline solid melting at about 136.5°–138° C.

Elemental analysis: Theory: C, 56.39; H, 6.88; N, 5.98; S, 6.84. Found: C, 56.09; H, 6.90; N, 6.24; S, 6.71.

Methoxyl determination: Theory: 19.88. Found: 18.79.

To a solution of 230 mg. of t-butyl ester prepared as described above in 5 ml. of pyridine was added dropwise over one-half hour, 1 equivalent of sodium hydroxide in 5.35 ml. of water. The addition was carried out at ice bath temperature. The solution was stirred under nitrogen for about 12 hours. The reaction solution was then allowed to warm to room temperature and was then diluted with 10 ml. of water. The diluted reaction mixture was freeze-dried to yield the mono sodium salt of the penicilloic acid half t-butyl ester as an orange solid.

The sodium salt was dissolved in 25 ml. of water and the solution cooled in an ice-bath to a temperature of about 0° to 5° C. To the cold solution was added 25 ml. of ethyl acetate and with stirring the mixture was acidified by the addition of 0.1N hydrochloric acid. The orange color passed into the ethyl acetate layer. The cold mixture was then extracted twice with 25 ml. portions of cold ethyl acetate. The extracts were combined and washed with water and then dried. The dried extracts were then evaporated in vacuo to yield 134 mg. of the methoxylated penicilloic acid half t-butyl ester as a yellow solid.

To a solution of 1 g. of the penicilloic acid half t-butyl ester in 250 ml. of methylene dichloride maintained at a temperature of −78° C. was added by dropwise addition over one half hour a solution of 454 mg. of dicyclohexylcarbodiimide in 80 ml. of dichloromethane. The solution was then stirred under nitrogen for 5 days at room temperature. After the initial addition of the dicyclohexylcarbodiimide a precipitate of dicyclohexylurea began to form. Following the reaction, the reaction mixture was concentrated by evaporation to a volume of 50 ml. and the concentrate allowed to cool at a temperatue of about 15° C. for 2 hours in the refrigerator. The concentrate was then filtered to remove the dicyclohexylurea and the filtrate was evaporated to dryness in vacuo to yield 931 mg. of an oily residue. The nuclear magnetic resonance spectrum of the residue showed the residue to be a mixture containing approximately 90% of t-butyl 2-[4-methoxy-5-oxo-2-(phenoxymethyl)-2-oxazolin-4yl]-5,5-dimethyl-4-thiazolidinecarboxylate with the remaining 10% being a mixture of dicyclohexylurea with a minor amount of a β-lactam containing product.

The residual oil of the composition described above was reacted for one-half hour at about room temperature with 40 ml. of 98% formic acid. The reaction mixture was then evaporated to remove the formic acid and the residue was dissolved in ethyl acetate. The ethyl acetate solution was then extracted twice with 10 ml. portions of a 5% solution of sodium bicarbonate. The washed ethyl acetate layer was dried over magnesium sulfate, and was then evaporated to provide 30 mg. of an oily neutral residue. The bicarbonate washes were combined and acidified and the acidified solution was extracted with ethyl acetate. The ethyl acetate extract was washed with cold water, was dried, and was then evaporated under reduced pressure to dryness to obtain a residual oil containing 6-methoxy-6-(2-phenoxyacetamido)-penicillanic acid as demonstrated in the standard agar dilution microbiological assay.

EXAMPLE 2

According to the procedures described by Example 1, the following 6-acylamido-6-methoxypenicillanic acids can be prepared with the corresponding non-methoxylated 6-acylamidopenicillanic acids:

6-methoxy-6-(2-phenylacetamido)penicillanic acid
6-methoxy-6-[2-(2-thienyl)acetamido]penicillanic acid,
6-methoxy-6-(2-phenylacetamido)penicillanic acid,
6-acetamido-6-methoxypenicillanic acid,
6-methoxy-6-propionamidopenicillanic acid,
6-methoxy-6-(2-hydroxy-2-phenylacetamido)-penicillanic acid,
6-methoxy-6-(2-amino-2-phenylacetamido)penicillanic acid,

We claim:
1. The compound of the formula

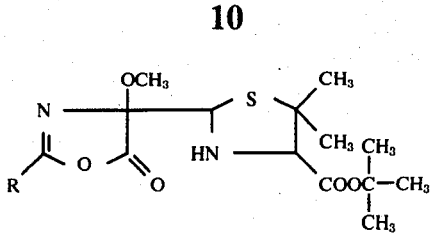

wherein R is $C_1$–$C_6$ alkyl, phenyl, halophenyl, $C_1$–$C_4$ alkylphenyl, $C_1$–$C_4$ alkoxyphenyl, or hydroxyphenyl, or a group of the formula

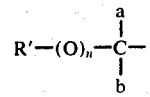

wherein
R' is α-thienyl, β-thienyl, α-furyl, β-furyl, phenyl, halophenyl, $C_1$–$C_4$ alkylphenyl, $C_1$–$C_4$ alkoxyphenyl or hydroxyphenyl,
$n$ is 0 or 1,
$a$ is hydrogen or $C_1$–$C_3$ lower alkyl,
$b$ is hydrogen, $C_1$–$C_3$ lower alkyl, hydroxy, amino, 2,2,2-trichloroethoxycarbonylamino, benzyloxycarbonylamino, ethoxycarbonylamino, or t-butyloxycarbonylamino;
with the limitation that when $n$ is 1, R' is phenyl or substituted phenyl and $b$ is hydrogen or $C_1$–$C_3$ lower alkyl.
2. The compound of claim 1 wherein R is phenoxymethyl.

* * * * *